(12) United States Patent
Goldfine et al.

(10) Patent No.: US 10,001,457 B2
(45) Date of Patent: Jun. 19, 2018

(54) PERFORMANCE CURVE GENERATION FOR NON-DESTRUCTIVE TESTING SENSORS

(75) Inventors: Neil J. Goldfine, Newton, MA (US); Yanko K. Sheiretov, Waltham, MA (US); Floyd W. Spencer, Albuquerque, NM (US); David A. Jablonski, Whitman, MA (US); David C. Grundy, Chelmsford, MA (US); Darrell E. Schlicker, Freeland, MI (US)

(73) Assignee: JENTEK SENSORS, INC., Waltham, MA (US)

( * ) Notice: Subject to any disclaimer, the term of this patent is extended or adjusted under 35 U.S.C. 154(b) by 992 days.

(21) Appl. No.: 13/451,128

(22) Filed: Apr. 19, 2012

(65) Prior Publication Data

US 2012/0271824 A1 Oct. 25, 2012

Related U.S. Application Data

(60) Provisional application No. 61/476,848, filed on Apr. 19, 2011.

(51) Int. Cl.
*G01N 27/82* (2006.01)
*G01N 27/90* (2006.01)
(Continued)

(52) U.S. Cl.
CPC .......... *G01N 27/90* (2013.01); *G01M 5/0033* (2013.01); *G01M 5/0091* (2013.01); *G01N 29/30* (2013.01)

(58) Field of Classification Search
CPC .. G01M 5/0033; G01M 5/0091; G01N 27/90; G01N 29/30
(Continued)

(56) References Cited

U.S. PATENT DOCUMENTS 5,345,514 A * 9/1994 Mahdavieh ........ G01N 27/9046
324/240
6,420,867 B1 * 7/2002 Goldfine et al. ............ 324/242
(Continued)

OTHER PUBLICATIONS

George A.Georgiou, Jacobi Consulting Limited "Probability of Detection(PoD) curves , Health and safety executive search report" , 454,2006.*
(Continued)

*Primary Examiner* — Yoshihisa Ishizuka
(74) *Attorney, Agent, or Firm* — Hamilton, Brook, Smith & Reynolds, P.C.

(57) ABSTRACT

Methods and apparatus for enhancing performance curve generation, damage monitoring, and improving non-destructive testing performance. Damage standards used for performance curve generation are monitored using a non-destructive testing (NDT) sensor during a damage evolution test performed with the standard. The evolution test may be intermittently paused to permit ground truth data to be collected in addition to the NDT sensor data. A damage evolution model may be used to estimate ground truth data during the intervening periods of the damage evolution test. The NDT sensor data and ground truth data are used to generate performance curves for the NDT system. Multiple sensors may be monitored at multiple locations on the damage standard and multiple damage evolution tests may be performed with multiple damage standards.

14 Claims, 12 Drawing Sheets

(51) Int. Cl.
*G01M 5/00* (2006.01)
*G01N 29/30* (2006.01)

(58) Field of Classification Search
USPC .................. 702/42, 181; 703/2; 324/242
See application file for complete search history.

(56) References Cited

U.S. PATENT DOCUMENTS

| | | | |
|---|---|---|---|
| 7,106,055 | B2 | 9/2006 | Goldfine et al. |
| 7,230,421 | B2 | 6/2007 | Goldfine et al. |
| 7,589,526 | B2 | 9/2009 | Goldfine et al. |
| 2007/0239407 | A1* | 10/2007 | Goldfine et al. .......... 703/2 |
| 2011/0000285 | A1* | 1/2011 | Biggs .............. G01N 11/16 73/54.41 |
| 2011/0060568 | A1 | 3/2011 | Goldfine et al. |
| 2011/0210724 | A1 | 9/2011 | Goldfine et al. |

OTHER PUBLICATIONS

Goldfine, N., et al., "Mapping and Tracking of Damage in Titanium Components for Adaptive Life Managemnet." Presented at the 10th Joint NASA/DoD/FAA Conference on Aging Aircraft, Palm Springs, CA, Apr. 16-19, 2007 (11 pages).

Goldfine, N., et al., Jentek Sensors, Inc., "Adaptive Damage Tolerance for Structural and Engine Components." Presented at the 37th ISTC Sample Fall Technical Conference, Seattle, WA, USA, Oct. 31-Nov. 3, 2005 (33 pages).

Jablonski, D., et al., Jentek Sensors, Inc., "Detection, monitoring, and measurement of short surface fatigue cracks in Al7075 and Ti-6Al-4V and prediction using a microstructure-based multistage fatigue model." Presented at the International Conference on Fatigue, Hyannis, MA, Sep. 19-24, 2010 (32 pages).

Jablonski, D., et al., Jentek Sensors, Inc., "Fatigue Assessment for Risk Management of Aerospace Components." to ASM Boston Chapter, Feb. 11, 2010 (30 pages).

Muller, C., et al., "POD (Probability of Detection) Evaluation of NDT Techniques for Cu-Canisters for Risk Assessment of Nuclear Waste Encapsulation," ECNDT 2006—Fr. 2.5.1 (22 pages).

United States of America, Department of Defense Handbook, Nondestructive Evaluation System Reliability Assessment, MIL-HDBK-1823A, Apr. 7, 2009 (171 pages).

* cited by examiner

FIG. 5B *Prior Art*

PERFORMANCE CURVE GENERATION FOR NON-DESTRUCTIVE TESTING SENSORS

RELATED APPLICATION

This application claims the benefit of U.S. Provisional Application No. 61/476,848, filed on Apr. 19, 2011.

GOVERNMENT SUPPORT

The U.S. Government has a paid-up license in this invention and the right in limited circumstances to require the patent owner to license others on reasonable terms as provided for by the terms of contract number FA8501-10-C-0032 awarded by United States Air Force.

The entire teachings of the above application are incorporated herein by reference.

BACKGROUND OF THE INVENTION

Non-destructive test (NDT) systems play a critical role in maintaining the health and safety of aircraft, power plants, distribution infrastructure, manufacturing operations, and other high value assets. NDT systems are used to provide information that reduces the risk of failure of such assets. For example, NDT systems may be used to determine the condition of a component. Knowing the current damage size in a component may be used to predict future damage size and determine whether the component should be replaced or can remain in service.

For risk analysis using NDT data to be effective, the confidence in information obtained from an NDT system must be ascertained. Thus, NDT systems are qualified by a reliability assessment to determine the confidence level that can be ascribed to the information they provide. One critical element of a reliability assessment is the probability of detection (POD), other elements include, for example, reproducibility. A POD study for an NDT system aims to answer the question "what is the largest damage size the NDT system can miss?"

How to answer this question accurately and efficiently has been a continuing challenge to the NDT community. POD studies generate performance curves that describe the POD as a function of damage size. To perform a POD study, damage standards are created or selected. Each damage standard has one or more inspection locations with damage of known size. A significant number of locations without damage are also utilized. The NDT system response at each inspection location on the damage standards, that is "â" ("a-hat") data, are recorded in relation to the damage size independently determined for the location, that is "a" or ground truth data. This "â versus a" provides the basis for computing performance curves, the associated parameters, confidence levels and the like.

Because the NDT system response is not completely predictive of the damage size, a maximum likelihood â response as a function of damage size, "a", is estimated from the â versus a data. This information may also be used to generate POD curves. The variance in the sensor response as a function of "a" may also be computed. Factors contributing to the variance include the repeatability of the inspection procedure, stability of the NDT system, the limitations of characterizing damage by a single "size" metric, and system noise.

MIL-HDBK-1823A, "Nondestructive Evaluation System Reliability Analysis, Apr. 7, 2009, published by the Department of Defense, provides a summary of developing POD studies in general and described the mechanics of some methods for generating performance curves from â versus a data, including the number of damage and no damage sites required.

SUMMARY OF THE INVENTION

Disclosed are methods and apparatus for enhancing performance curve generation, damage monitoring, and improving non-destructive testing performance. Damage standards used for performance curve generation may be monitored using a non-destructive testing sensor during a damage evolution test performed with the standard. The evolution test may be intermittently paused to permit ground truth data to be collected in addition to the NDT sensor data. A damage evolution model may be used to estimate ground truth data during the intervening periods of the damage evolution test. The NDT sensor data and ground truth data are used to generate performance curves for the NDT system. Multiple sensors may be monitored at multiple locations on the damage standard and multiple damage evolution tests may be performed with multiple damage standards. The NDT sensors may have multiple sense elements arranged along a damage growth direction to achieve a substantially linear sensor response over a wider range of damage sizes than could be achieved by a single sensor alone.

One aspect relates to a method of generating a probability of detection (POD) curve. The method comprising acts of (a) placing a sensor proximal to a damage standard; (b) loading the damage standard to initiate and grow damage of interest at a location observed by the sensor; (c) monitoring a response of the sensor during the loading; (d) measuring ground truth data for the damage of interest; and (e) generating the POD curve based at least in part on the response of the sensor during the loading and the ground truth data.

In some embodiments the method further comprises acts of defining an acceptable confidence based criterion for at least one parameter of the POD curve; repeating acts (a), (b), (c) and (d) for a sufficient number of damage standards to satisfy the acceptable confidence based criterion for at least one parameter of the POD curve; and verifying the acceptable confidence based criterion for the at least one parameter of the POD curve is met or exceeded.

In some embodiments the acceptable confidence based criterion is predetermined based on a risk analysis for an intended application of the POD curve.

In some embodiments the intended application is risk based life management of a critical component using remaining life estimation that includes a non-destructive testing method represented by the POD curve.

In some embodiments the at least one parameter comprises a damage level at a 90% probability of detection point in the POD curve that has an associated 95% confidence level.

In some embodiments the damage of interest is a fatigue crack, and loading is cyclical at a predetermined load level that is representative for a component of interest.

In some embodiments the loading is dynamic loading, the method further comprises suspending the dynamic loading and, during such suspension, obtaining ground truth data at the location, and the generating of the POD curve is further based on the obtained ground truth data.

In some embodiments the ground truth data is obtained by an acetate replica.

In some embodiments the ground truth data is augmented by estimating ground truth using a damage growth model and the ground truth data.

In some embodiments the generating of the POD curve is further based on non-destructive testing results from field service components using essentially the same inspection procedure and sensor used on the damage standards.

In some embodiments the sensor is an eddy current sensor and the eddy current sensor is placed at a fixed position throughout acts (b) and (c).

In some embodiments the sensor is an eddy current sensor and act (c) comprises scanning the eddy current sensor over the location.

Another aspect relates to another method. The method comprises placing a first sensor to observe damage at a first location on a damage standard; placing a second sensor to observe damage at a second location on the damage standard; loading the damage standard; at a plurality of times during the loading, measuring first responses of the first sensor and second responses of the second sensor; estimating parameters of a probability of detection (POD) curve based at least in part on the first and second responses.

In some embodiments the damage to be observed is cracking and the first and second responses are recorded during a period of the loading where a static load is applied to the damage standard.

In some embodiments the damage to be observed is cracking and the first and second responses are recorded during loading with a sufficient data acquisition rate to segment the responses based on a degree of loading.

In some embodiments the first and second sensors are eddy current sensors.

In some embodiments the first and second locations on the damage standard are substantially identical.

In some embodiments the first location comprises material adjacent to a hole in the damage standard and the first sensor has a two sensing elements that are located on sides of the hole transverse to a loading direction.

In some embodiments the measuring comprises measuring first and second responses at a plurality of frequencies, and the estimating of the parameters of the POD curve based at least in part on the first and second responses comprises estimating crack depth from each of the first and second responses at the first location and second location, respectively.

In some embodiments the first location is a layer of a multiple layered construct representing an aircraft structure.

Another aspect relates to a system comprising a test part and a sensor. The sensor, proximal to the test part, having a field source and at least two sensing elements, the at least two sensing elements located to monitor damage growth along an anticipated damage growth path on the test part such that a sensor response is substantially linear with respect to actual damage level.

In some embodiments the at least two sensing elements comprise a first sensing element and a second sensing element and the system further comprises a measurement instrument to measure a first response of the first sense element and a response of the second sensing element and to combine the first and second response into the substantially linear sensor response.

In some embodiments first response is substantially linear for a first range of smaller actual damage levels, and the second response is substantially linear for a second range of larger actual damage levels, and the substantially linear first range for the first response approximately abuts the substantially linear second range for the second response.

In some embodiments the at least two sensing elements are substantially a same size.

In some embodiments the sensor is proximal a hole on the test part and the at least two sensing elements comprise a first sensing element at a first radius from the hole and a second sensing element at a second radius from the hole larger than the first radius.

In some embodiments the second sensing element is larger than the first sensing element in proportion to the second radius relative to the first radius.

In some embodiments the sensor is an eddy current sensor where the field source is a first drive conductor and the at least two sensing elements comprise secondary windings.

In some embodiments the sensor is an ultrasonic sensor where the field source is an ultrasonic transducer and the at least two sensing elements comprise an ultrasonic detector.

In some embodiments the test part is representative of a component of in an aircraft.

Yet another aspect relates to a system comprising a database, a non-transitory computer-readable storage medium and a processor. The database has a plurality of spatially registered sensor responses obtained from a set of one or more damage standards, the database relating each of at least a subset of said sensor responses to a respective damage size, wherein the plurality of sensor responses comprise (i) sensor responses obtained at different times at a same location from a damage standard in the set and (ii) sensor responses obtained at different locations from a damage standard in the set. The non-transitory computer-readable storage medium stores computer-executable instructions. The processor is configured to execute the computer-executable instructions to perform a method. The method comprises acts of accessing the database; estimating, for each of the at least a subset of the plurality of sensor responses, a feature of the sensor response that is correlated with the respective damage size; and processing the estimated features and the respective damage size to estimate parameters of a performance curve and confidence intervals associated with the performance curve.

In some embodiments the sensor further comprises a sensor for interrogating the damage standards; a spatial encoder to generate a relative position of the sensor; and an instrument configured to record the relative position of the spatial encoder and measure sensor responses as the sensor is physically scanned across a damage standard from the set, and further record the relative position and sensor responses to the database.

In some embodiments the method further comprises spatially registering the sensor responses obtained at different times at the same location from the same damage standard by identifying common spatial features in both sensor responses and shifting the sensor responses to align the common spatial features.

In some embodiments the system further comprises a damage standard loading apparatus to load the damage standard, wherein the instrument further records a load applied to the damage standard during measurement of the sensor response.

In some embodiments the damage standard loading apparatus is configured to apply a static load during measurement of the sensor responses.

In some embodiments the instrument is configured to record sensor responses at a plurality of static loads from a damage standard without intervening damage evolution.

In some embodiments the method further comprises combining the sensor responses at two different static loads.

In some embodiments the sensor is an eddy current sensor.

In some embodiments the database comprises sensor responses that are spatially registered in at least two directions.

The foregoing is a non-limiting summary of the invention, which is defined by the attached claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 5B is a plot illustrating a performance curve with confidence bounds;

DETAILED DESCRIPTION OF THE INVENTION

The inventors have recognized and appreciated that constructing a database of "â versus a" data may be accelerated and enhanced by obtaining multiple NDT sensor responses at each damage location on one or more damage standards. Not only is NDT system data (i.e., â data) taken at the final damage size for the damage standard (i.e., at the end of the damage evolution test), but NDT system data is also acquired during the damage evolution test. That is, during the test by which damage is grown in the damage standard NDT system data is taken occasionally or continually. An NDT sensor may be continually scanned (e.g., scanned at scheduled intervals through the test) over a region of interest, or multiple sensors may be placed on the damage standard to record data at the damage locations during the test. In some embodiments, ground truth data is intermittently collected. By recording NDT data during the damage evolution test of the damage standard the "â versus a" database may more rapidly be populated.

The inventors have further recognized and appreciated that sensors with multiple sensing elements along a damage growth path may be used to extend the uniquely identifiable range of damage sizes. Specifically, a first sensing element of the sensor proximal to a damage initiation site will have a change in sensor response early in the evolution of damage from the initiation site. At some point however, the damage may saturate the sense element response or the sensor response may become double valued if damage above a certain size is considered or the sensor response may only be sensitive to damage size changes over a limited range. The inventors have recognized and appreciated that providing a second sensing element along the damage growth path but further from the damage initiation site will extend the damage size that may be observed unambiguously. Thus the range of damage sizes for which a monotonic change in sensor response is observed is increased while maintaining good sensitivity to defects.

Figure 1:
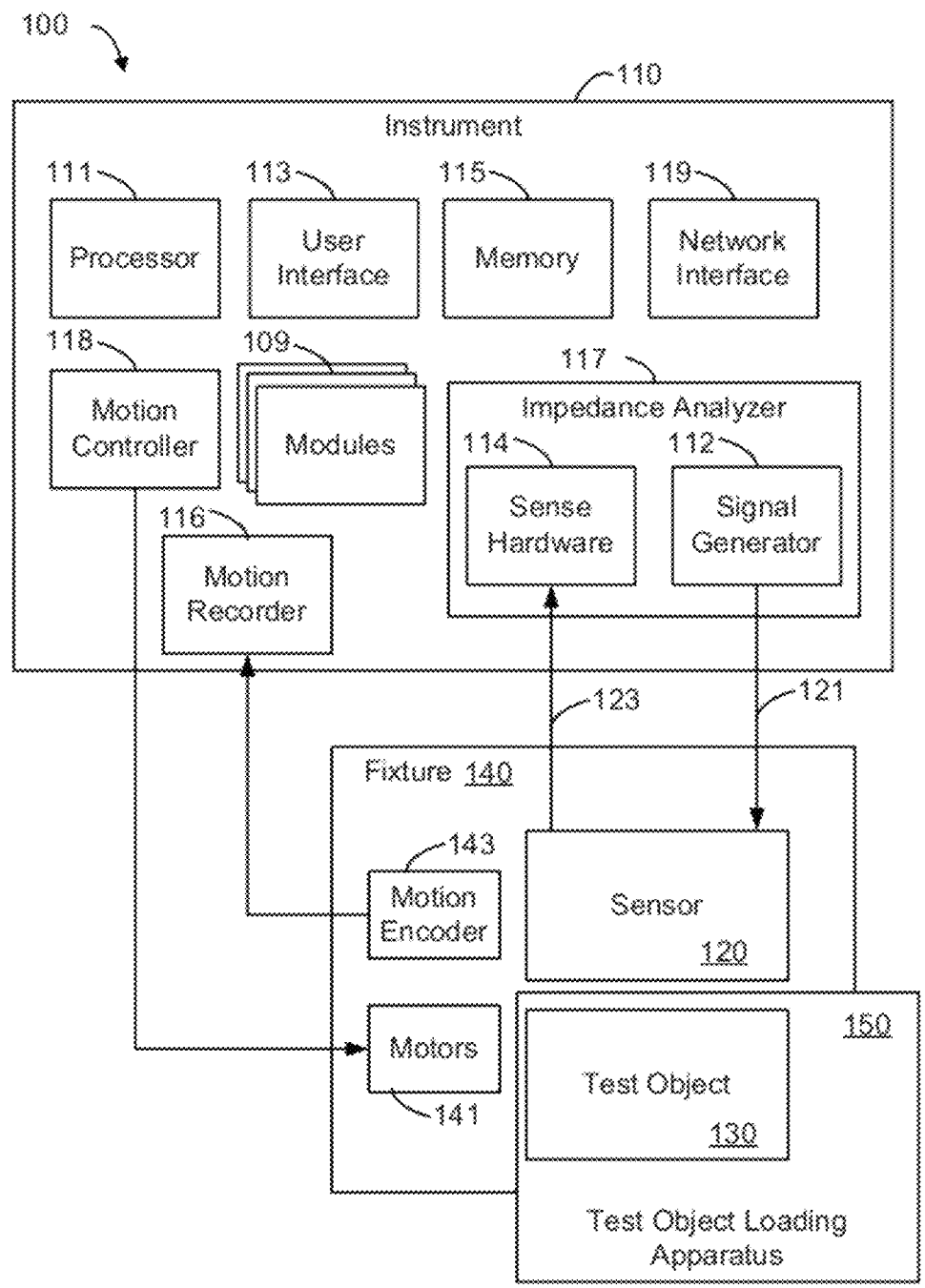
FIG. 1 is a block diagram of an NDT system according to some embodiments.

With this appreciation, attention is now turned to FIG. 1 which shows a block diagram of a NDT system 100 for inspecting a test object 130. Test object 130 may be a component, subcomponent, a feature thereof, a damage standard (e.g., fatigue coupon), or any other object to be tested by system 100.

NDT system 100 includes an instrument 110 and a sensor 120. Instrument 110 is configured to provide excitation signals 121 to sensor 120 and measure the resulting response signals 123 of sensor 120. Measured response signals 123 may be processed to estimate properties of interest, such as electrical properties (e.g., conductivity, permeability, and permittivity), geometric properties (e.g., thickness, sensor lift-off), material condition, or any other suitable property or combination thereof. Such material property estimates may represent the response of the NDT system, â.

Instrument 110 may include a processor 111, a user interface 113, memory 115, an impedance analyzer 117, and a network interface 119. Though, in some embodiments of instrument 110 may include other combinations of components. While instrument 110 is drawn as a single block, it should be appreciated that instrument 110 may be physically realized as a single "box"; multiple, operably-connected "boxes", or in any other suitable way. For example, in some embodiments it may be desired to provide certain components of instrument 110 as proximal to sensor 120 as practical, while other components of instrument 110 may be located at greater distance from sensor 120.

Processor 111 may be configured to control instrument 110 and may be operatively connected to memory 115. Processor 111 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, distributed network of processors, or any suitable processing device. In some embodiments, processor 111 comprises one or more processors, for example, processor 111 may have multiple cores and/or be comprised of multiple microchips.

Memory 115 may be integrated into processor 111 and/or may include "off-chip" memory that may be accessible to processor 111, for example, via a memory bus (not shown). Memory 115 may store software modules that when executed by processor 111 perform desired functions. Memory 115 may be any suitable type of non-transient computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 110 may have one or more functional modules 109. Modules 109 may operate to perform specific functions such as processing and analyzing data. Modules 109 may be implemented in hardware, software, or any suitable combination thereof. Memory 115 of instrument 110 may store computer-executable software modules that contain computer-executable instructions. For example, one or more of modules 109 may be stored as computer-executable instructions in memory 115. These modules may be read for execution by processor 111. Though, this is just an illustrative embodiment and other storage locations and execution means are possible.

In some embodiments, modules 109 include a sensor data processing module that estimates properties of test object 130. The sensor data processing module may utilize property grids stored in memory 115. Property grids are multi-dimensional pre-computed databases that relate one or more sensor measurements (e.g., frequency transimpedance measurements to properties to be estimated). The sensor data processing module may take the property grids and sensor data and, using grid methods, estimate material properties.

User interface 113 of instrument 110 may include devices for interacting with a user of NDT system 100. Devices of the user interface may include, by way of example and not limitation, a keypad, pointing device, camera, display, touch screen, audio input and audio output, or any other suitable interface for interacting with the user.

Network interface 119 may be any suitable combination of hardware and software configured to communicate over a network. For example, network interface 119 may be implemented as a network interface driver and a network interface card (NIC). The network interface driver may be configured to receive instructions from other components of instrument 110 to perform operations with the NIC. The NIC provides a wired and/or wireless connection to the network. The NIC is configured to generate and receive signals for communication over network. In some embodiments, instrument 110 is distributed among a plurality of networked computing devices. Each computing device may have a network interface for communicating with other the other computing devices forming instrument 110. Cabling for the network may be parallel, multiplexed, or a hybrid of the two with modular and reconfigurable constructs.

Instrument 110 provides excitation signals for sensor 120 and measures the response signal from sensor 120 using impedance analyzer 117. Impedance analyzer 117 may contain a signal generator 112 and sense hardware 114.

Signal generator 112 provide an excitation signal to sensor 120. In some embodiments signal generator 112 may be configured to provide multiple excitation signal outputs. Signal generator 112 may utilize a multiplexer to time-share the signal generation function among the multiple outputs or may have parallel signal generation hardware to provide multiple output signals simultaneously. Multiple outputs may be used to drive multiple sensors, or a sensor with multiple drive elements. Signal generator 112 may provide a suitable voltage and/or current waveform for driving sensor 120. For example, signal generator 112 may provide a sinusoidal signal at one or more selected frequencies, a pulse, a ramp, or any other suitable waveform.

Sense hardware 114 may comprise one or more sensing channels for measuring a sensing element response. In some embodiments, sense hardware 114 has a plurality of parallel channels so that multiple sense channels may be simultaneously measured. Multiplexing may be used where the number of sense elements, for example, exceeds the number of sensing channels available in sense hardware 114. Though, other configurations may be used. Sense hardware 114 may measure sensor transimpedance for one or more excitation signals at on one or more sense elements of sensor 120. It should be appreciated that while transimpedance (sometimes referred to simply as impedance), may be referred to as the sensor response, the way the sensor response is represented is not critical and any suitable representation may be used. In some embodiments, sense hardware 114 also measures a property of the output of signal generator 112. For example, sense hardware 114 may measure the voltage or current of the drive signal provided by signal generator 112. Once sense hardware 114 has measured the sensor response, the sensor response may, for example, be stored in memory 115.

Sensor 120 may be any suitable sensing technology or combination of sensing technologies for interrogating test object 130. Sensor 120 may be, for example and not limitation, an eddy-current sensor, a dielectrometry sensor, or an ultrasonic sensor. In some embodiments, sensor 120 is a linear drive eddy-current sensor such as an MWM® or MWM®-Array available from JENTEK Sensors, Inc., Waltham, Mass. In another embodiment, sensor 120 is an interdigitated dielectrometry sensor or a segmented field dielectrometry sensor such as the IDED® sensors also available from JENTEK Sensors, Inc. Sensor 120 may have a single or multiple sensing and drive elements. Sensor 120 may be scanned, fixtured to, mounted on, or embedded into test object 130.

As discussed above in connection with sensor 120, a fixture 140 may be used to position sensor 120 with respect to test object 130. Where sensor 120 requires close proximity to test object 130, such as for a ultrasonic test sensor or eddy current test sensor, fixture 140 will closely conform sensor 120 with test object 130. Fixture 140 may also be configured to hold test object 130 in a predetermine position. Fixture 140 may be a stationary fixture, manually controlled, motorized fixture, or any suitable combination thereof. For scanning applications where fixture 140 moves sensor 120 relative to test object 130, it is not critical whether sensor 120 or test object 130 is moved, or if both are moved to achieve the desired scan.

NDT system 100 may have one or more motors 141 that are controlled by motion controller 118. Motion controller 118 may control fixture 140 to move sensor 120 relative to test object 130 during an inspection procedure. Though, in some embodiments, relative motion between sensor 120 and test object 130 is controlled by the operator directly (e.g., by hand). Regardless of whether motion is controlled by motion controller 118 or directly by the operator, position encoders 143 and motion recorder 116 may be used to record the relative positions of sensor 120 and test object 130. The position information recorded by motion recorded 116 may be used to spatially register the sensor data obtained by instrument 110 may therefore be spatially registered with the test object 130.

In some embodiments, test object 130 is loaded using a loading apparatus 150. That is test object 130 is mechanically stressed by loading apparatus 150. Loading apparatus 150 may impose a static load, a dynamic load, loading in in one or more orientations, loading in a linear direction, bending loads, torsional loading, or any other type of loading or combination thereof. Loading apparatus 150 may be configured to vary the load applied to test object 130. For example, low-cycle or high-cycle fatigue may be administered with intermediate pauses to permit inspection of test object 130. In some embodiments loading apparatus 150 is a servo-hydraulic fatigue testing machine, servo-pneumatic fatigue testing machine, or any other suitable apparatus for loading test object 130. In some embodiments loading is achieved in alternate ways such as during field operation of the test object (e.g., an aircraft component during flight). Loading apparatus 150 may be used during a damage evolution test of a damage standard, for example, to generate fatigue cracks in the damage standard.

Figure 2:
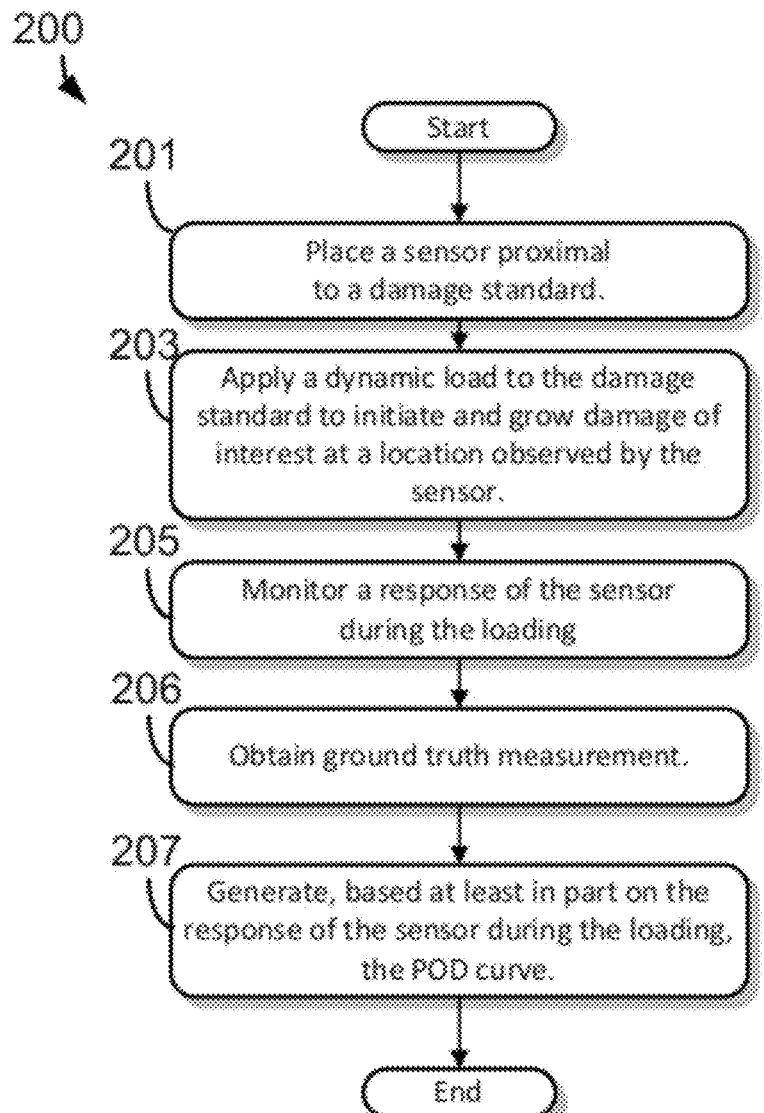
FIG. 2 is a flow diagram of a method for generating a performance curve using an NDT system according to some embodiments.

Having described NDT system 100, a method 200 for generating a performance curve with the system is described in connection with FIG. 2. Method 200 may be used to generate performance curves from damage standards for the NDT system used for inspection of a target component. In some embodiments, method 200 is used to qualify NDT system 100 for inspection of a target component. In such embodiments, non-conflicting principles of reliability analysis known in the art (e.g., MIL-HDBK-1823A) may be used in conjunction with method 200. For example, the damage standards, sensor, and inspection procedure may be substantially similar to those used or planned for the actual target component inspection. By observing such principles the performance curves resulting from method 200 will have better accuracy when used to interpret inspection results on the target component.

At step 201 of method 200 a sensor is placed proximal to a damage standard. The sensor may be positioned in ways described above in connection with NDT system 100. For example, the sensor may be mounted to the damage standard, held in place with a fixture or an adhesive, or fixtured to scan a surface area of the damage standard. Though any suitable technique for placing the sensor may be used. In some embodiments, the sensor is of the same design used for inspection of the target component. Again, procedures consistent with the target inspection will improve the relevance of the performance curves generated by method 200. The sensor may be placed proximal to the damage standard in ways similar to the inspection of the target component. For example, the sensor may have the same orientation with respect to the geometry of the inspection region on both the damage standard and the target component. Other properties controlled may be specific to the sensor technology. For example, the sensor lift-off of an eddy-current sensor will have a substantial effect on the inspection sensitivity. Lift-off should be within the range that will be achieved on the target component during field/depot inspections with the NDT system. If step 201 is performed with substantial bias towards low or high lift-offs relative to those achieved on the target component, the performance curves may be more or less favorable than what is to be expected in practice.

Figure 5A:
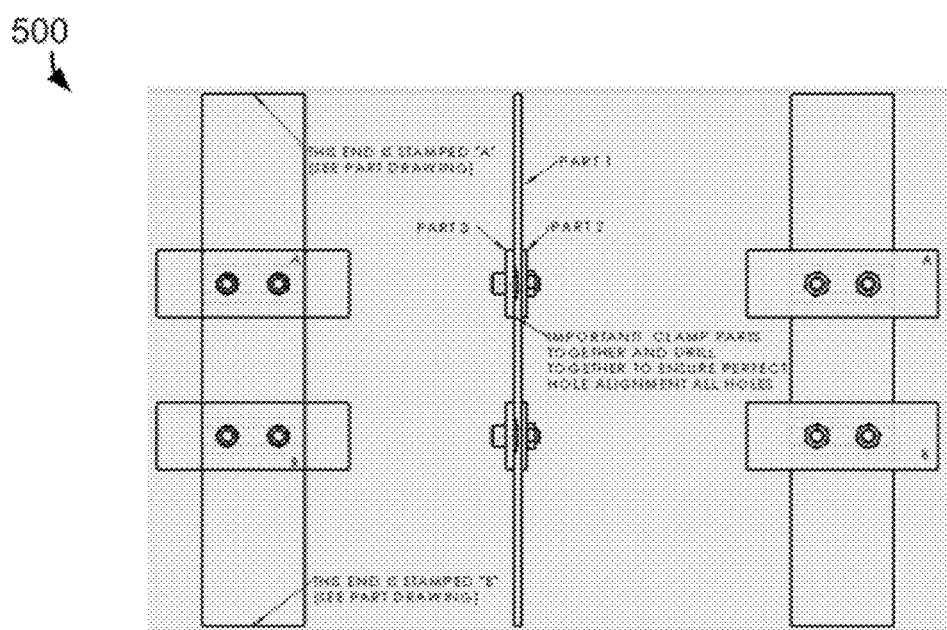
FIG. 5A is a diagram of a damage standard according to some embodiments.

Any suitable damage standard may be used for method 200. FIG. 5A illustrates an example of a damage standard 500. Standard 500 is a metal plate with 4 bolt hole locations that will have high stress regions when the damage standard is fatigued. The damage standard in this example is intended to be fatigued in tension with ends "A" and "B" gripped in opposite ends of a servo-hydraulic fatigue machine. As another example, the damage standard may be a multiple layered construct representing an aircraft structure. Note that damage of interest may be formed in any of the layers, depending on the damage standard design, the loading applied, and the like. A description of fabrication techniques for damage standard samples may be found in U.S. Pat. No. 7,106,055 titled "Fabrication of samples having predetermined material conditions" by Goldfine et al. and U.S. Pat. No. 7,230,421 titled "Damage standard fabrication with attached sensor" by Goldfine et al., both of which are incorporated by reference in their entirety.

At step 203 a load is applied to the damage standard. The damage standard may be dynamically loaded, for example, in low-cycle or high-cycle fatigue, or with any other suitable dynamic loading sequence. The load may be applied, for example, by a loading apparatus such as loading apparatus 150, described above in connection with FIG. 1. The damage standard may be designed such that the damage standard will experience high stresses in the region of interest that mimic the loading experienced by the target component during service. For example, the loading may be simulated by a periodic load cycling of the damage standard.

At step 205 the response of the sensor is monitored during the loading step 203. The sensor response may be monitored continually or occasionally during the loading and recorded. For example, the sensor response may be recorded at periodic intervals or the response of the sensor may be used to schedule the next recording of data. In one embodiment, sensor response are recorded more often after the sensor response indicates damage growth.

As the damage evolution test steps 203 and 205 proceeds, the damage standard may develop damage at one or more locations. Because the sensor response may depend on both the growth of damage in the damage standard and also the load applied during when the sensor response is measured, method 200 may optionally be performed to permit the contribution of the applied load to be removed or held constant during measurement of the sensor response. In some embodiments, the sensor response is recorded for the same load level on the damage standard that the target component will experience during its inspection. For example, if the target component will not be under load during inspection, the sensor response may be recorded at no load.

In some embodiments the load is recorded in connection with the sensor response. The data rate for obtaining a sensor measurement may be sufficiently fast that a sensor response at essentially a static load level may be recorded.

The damage evolution test steps 203 and 205 may continue until some termination criterion is met. For example, the damage standard may break, the damage may reach a point that the NDT sensor is saturated, the damage level may extend beyond the linear range of the sensor response, the damage may reach a prescribed size, or the loading sequence may have been completed (e.g., a predetermined number of cycles). Though, any suitable end criteria may be used.

At step 206 ground truth data is measured for the damage. For example, after the damage evolution test is complete, the damage standard may be inspected using an alternative technique to estimate the damage size. For example, in some embodiments the damage is a crack and the damage size is a crack length. The crack length may be estimated from acetate replicas, optically, using a scanning electron microscope (SEM), or any other suitable technique for determining the ground truth. In some embodiments, optical examination, or acetate replication may be performed while the damage standard is under load. Other damage modalities and potential sizing mechanism include, for example, fractography to determine crack length and crack depth. Once collected, the ground truth data may be associated with sensor response data.

At step 207 a performance curve is generated based at least in part on the response of the sensor during loading and the respective ground truth data (i.e., the â versus a data). The performance curve may be generated in any suitable way from the â versus a data.

In some embodiments steps 201, 203, 205, and 206 are repeated for multiple damage standards prior to generating the performance curve to provider a richer and more diverse set of â versus a data.

Figure 3:
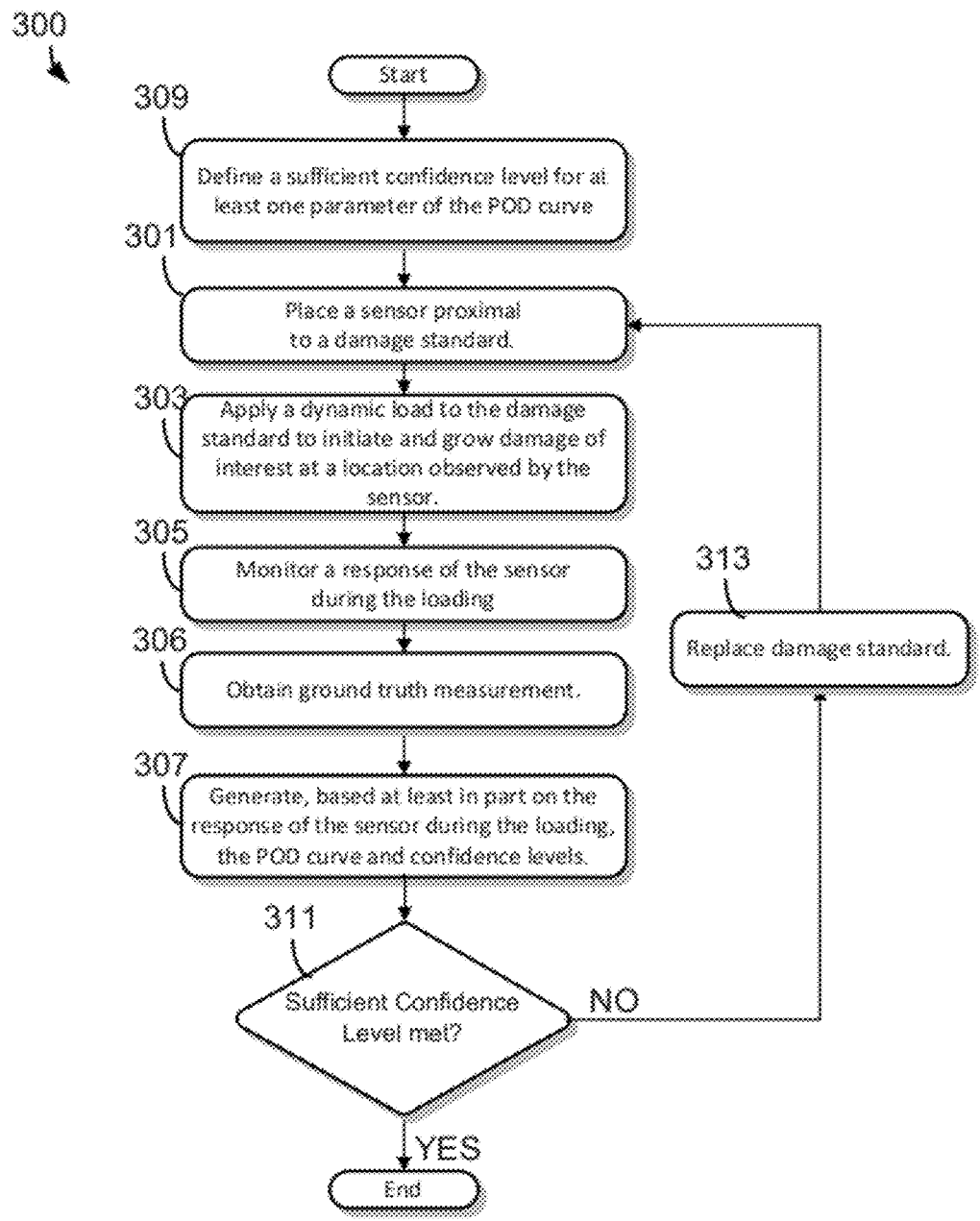
FIG. 3 is a flow diagram of another method for generating a performance curve using an NDT system according to some embodiments.

In some embodiments method 200 is enhanced to provide a performance curve with a sufficient confidence level using the fewest necessary damage standards. Such a method, method 300, is described in connection with FIG. 3.

Method 300 includes a step 309, defining a sufficient confidence level (i.e., an acceptable confidence based criterion) for at least one parameter of the POD curve. For example, the parameter may be the $a_{90}$ damage size (i.e., the damage size that is detected with 90% probability of detection). The acceptable confidence based criterion may be that an upper 95% confidence bound on $a_{90}$, designated $a_{90/95}$, be no larger than a specified size, or that the difference $a_{90/95} - a_{90}$ be within some limit. Plot 520 in FIG. 5B illustrates a POD curve 521 with the $a_{90/95}$ damage level labeled. (Note that FIG. 5B is a simplified version of Figure G-7 of MIL-HDBK-1823A. Any suitable parameters may be used individually or in any suitable combination as the parameter of interest. The acceptable criterion and its associated confidence level (such as the "confidence bounds" or "confidence interval") for the parameter may be computed, for example, using the likelihood ratio method based on the asymptotic $\chi^2$ (chi-square) distribution of the log-likelihood or the Wald method. Though, any suitable method in determining the confidence level may be used. Plot 500 also indicates the 95% confidence bounds 523 on POD curve 521.

Method 300 steps 301, 303, 305, 306, and 307 may be performed in ways similar to those described in connection with steps 201, 203, 205, 206, and 207, respectively, of method 200.

At step 311 a determination is made whether the confidence based criterion defined at step 301 has been satisfied. The determination of whether the criterion has been met may be determined from the performance curve statistics and may be expressed as an actual confidence level achieved for the parameter or as a restatement of the parameter criterion achieved at a specified confidence level. The actual confidence level may be determined from the performance curve statistics and compared to the confidence based criterion set at step 309.

If it is determined at step 311 that the sufficient confidence level has been reach (i.e., that the confidence based criterion has been satisfied), method 300 ends. Though, in some embodiments additionally criteria may be checked at step 311. For example, a minimum number of damage standards to be used in data generation may be set and the POD parameter of interest defined with respect to all the damage standards. In such case method 300 ends when all termination criteria are satisfied at step 311.

If it is determined at step 311 that the sufficient confidence level has not yet been reached (i.e., that the confidence based criterion has not yet been satisfied), method 300 continues to step 313 wherein the damage standard is replaced. Method 300 then repeats steps 301, 303, 305, and 306 with the replacement damage standard. Note that various conditions of the test may be altered to reflect realistic variations experienced during inspection of the target component. For example, different combinations of sensors (typically of the same design), instruments, and the like may be used. Also, the termination conditions for the damage evolution test (steps 303 and 305) may be modified. For example, the damage evolution test may terminate at a larger or smaller damage size. Termination may also be invoked if the performance curves indicate at a high confidence level that the NDT system is not currently capable of satisfying the specified acceptance criterion.

At step 307 the performance curves are regenerated using the data collected from the replacement damage standard and the preceding damage standards from which data were collected in earlier iterations of method 300. This process continues until the exit criteria at step 311 are met and method 300 ends.

Figure 4:
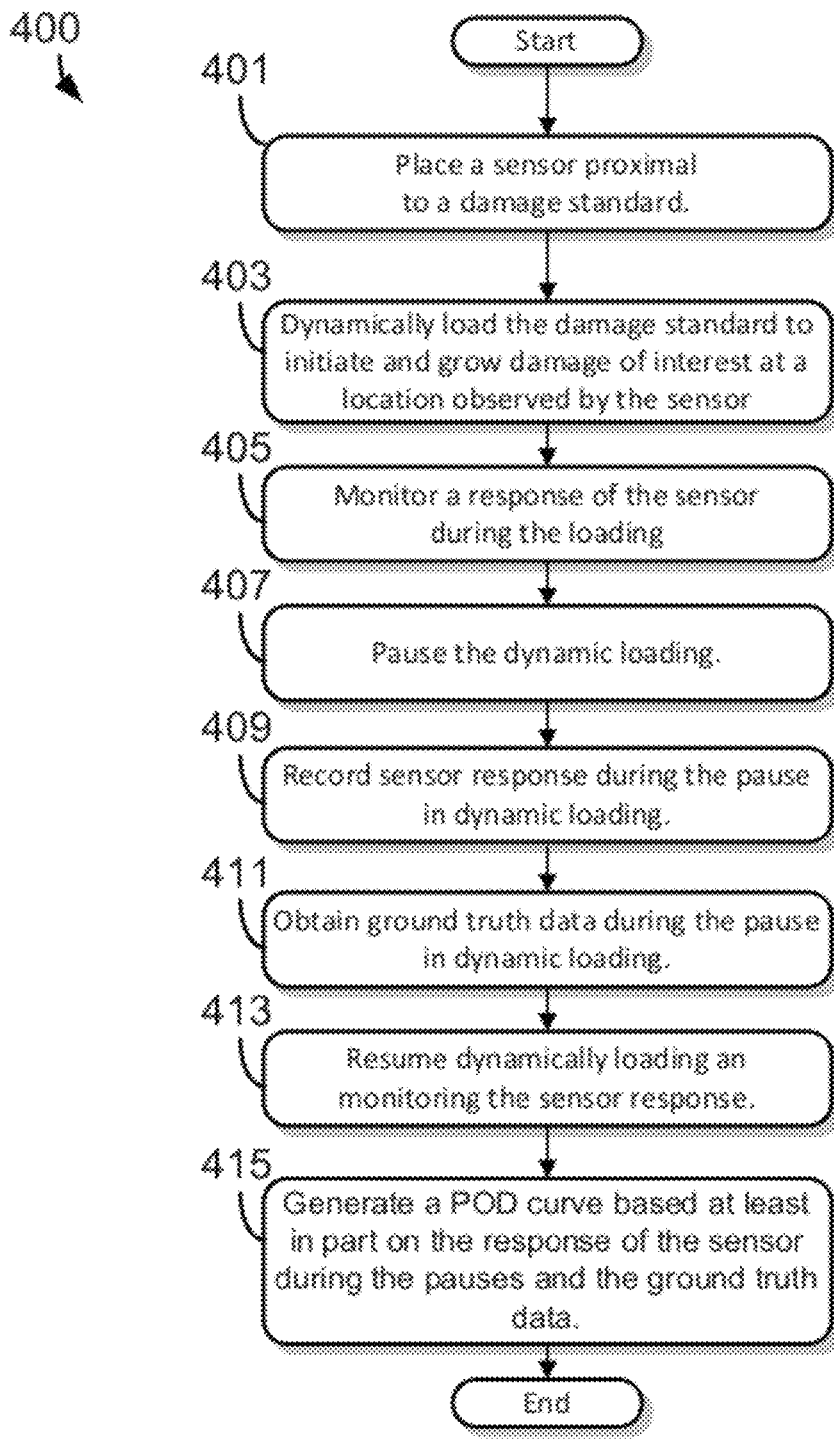
FIG. 4 is a flow diagram of yet another method for generating a performance curve using an NDT system according to some embodiments.

Method 400, described in connection with FIG. 4 is a method similar to method 200 with additional steps taken to acquire intermittent ground truth data during the damage evolution test.

Steps 401, 403, and 405 of method 400 are similar to steps 201, 203, and 205, respectively of method 200. These steps of method 400 may be performed in ways similar to those described with the respective step of method 200. Though, in method 400 the damage standard is dynamically loaded at step 403.

At step 407 the dynamic loading is paused. During the pause in dynamic loading either no load or a static load may be applied to the damage standard. For example, the predetermined static load may be between zero and the peak dynamic load. The point in the dynamic loading process may be recorded for future use. For example, in a low cycle fatigue damage evolution test, the number of cycles into the test at the time of the pause may be recorded.

At step 409, during the pause in dynamic loading the sensor response is recorded. As noted above, the sensor may be, for example, at a fixed position or scanned as the sensor response is recorded.

At step 411, also during the pause in dynamic loading ground truth data is obtained. The ground truth data may be obtained using acetate replication, SEM, or any other suitable methodology for recording the ground truth data.

In some embodiments, the damage standard may be removed from the loading apparatus for performance of steps 409 and 411, though, in some other embodiments, steps 409 and 411 are performed with the damage standard in place. Also steps 409 and 411 may be performed at multiple static loads. For example, steps 409-411 may be performed both as no load is applied and as a "high" static load is applied. It is noted that for some technologies used for ground truth data recording, placing the damage standard under load may improve the accuracy of the ground truth data.

In some embodiments performance of step 411 may require removal of the sensor, accordingly step 401 may need to be repeated prior to performance of step 413. In some embodiments, the sensor is removed and then replaced at the same location. Tooling may be used to ensure that the sensor is repositioned at the same location. In some embodiments, a method is used to reset the sensor data to align the response before and after the sensor is removed and remounted.

At step 413 the dynamic loading of the damage standard is resumed. Monitoring of the sensor response during dynamic loading with the sensor is also resumed.

In some embodiments steps 407, 409, 411, and 413 are repeated intermittently during the damage evolution test. For example, the steps may be repeated periodically, randomly, based on the sensor response, or scheduled/initiated in any other suitable way. In this way intermittent ground truth data may be acquired.

The intermittent ground truth data and any data from destructive testing (e.g., fractography) of the final state may be input into a damage evolution model along with the information representing the point in time in the damage evolution test at which the data were taken. The damage evolution model may then be used to estimate the ground truth data at times between the pauses—that is at times when the damage standard was being dynamically loaded and only direct sensor measurement data is available.

Figure 5C:
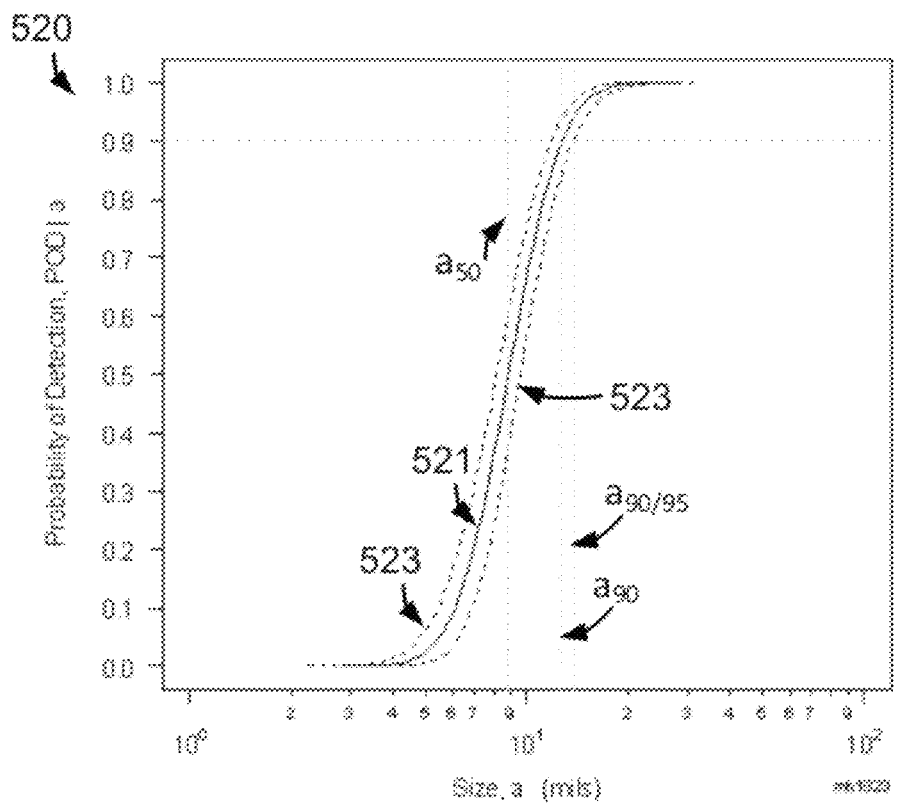
FIG. 5C is a plot illustrating the use of a damage evolution model to estimate ground truth data according to some embodiments.
Figure 5C:
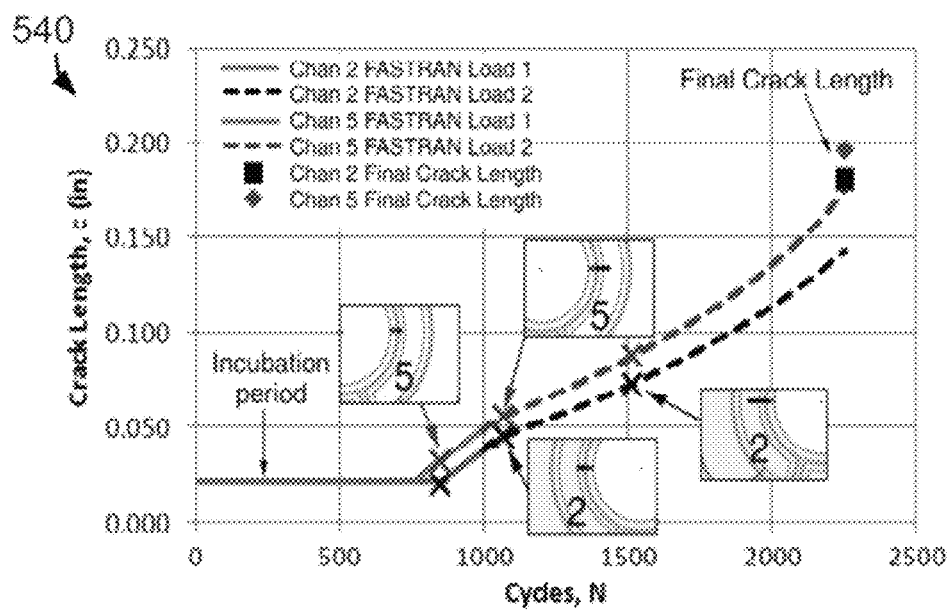

Plot 540 in FIG. 5C illustrates estimation of damage size (here crack length) using a damage evolution model and based on the ground truth data recorded at various points in the damage evolution test. Plot 540 shows an example where ground truth data were acquired at about 800 fatigue cycles, 1,100 fatigue cycles and 1,500 fatigue cycles. In this example, the crack length during the intervening periods is predicted using a Fatigue Crack Growth Structural Analysis (FASTRAN II) computer program and plotted in plot 540.

At step 415 a performance curve is generated based at least in part on the response of the sensor recorded at step 409 and the ground truth data obtained at step 411. In embodiments, where multiple pauses are made to take static sensor data and ground truth data during the damage evolution test, this additional data may be used in generation of the POD curve. Further, in embodiment, where a damage evolution model is used to estimate ground truth data at time between the pauses, the estimated information in combination with the monitored sensor responses may be used for POD curve generation.

In some embodiments, steps 401-413 are repeated for one or more additional damage standards. The performance curves may be generated incorporating data from the additional damage standards in similar ways. In some embodiments, the number of additional damage standards is determined based on confidence based criteria associated with one or more parameters of the POD curve (see method 300).

In some embodiments, the sensor is not monitored when the damage standard is dynamically loaded. Accordingly steps 401, 405, and 413 may be omitted in such embodiments.

Figure 6A:
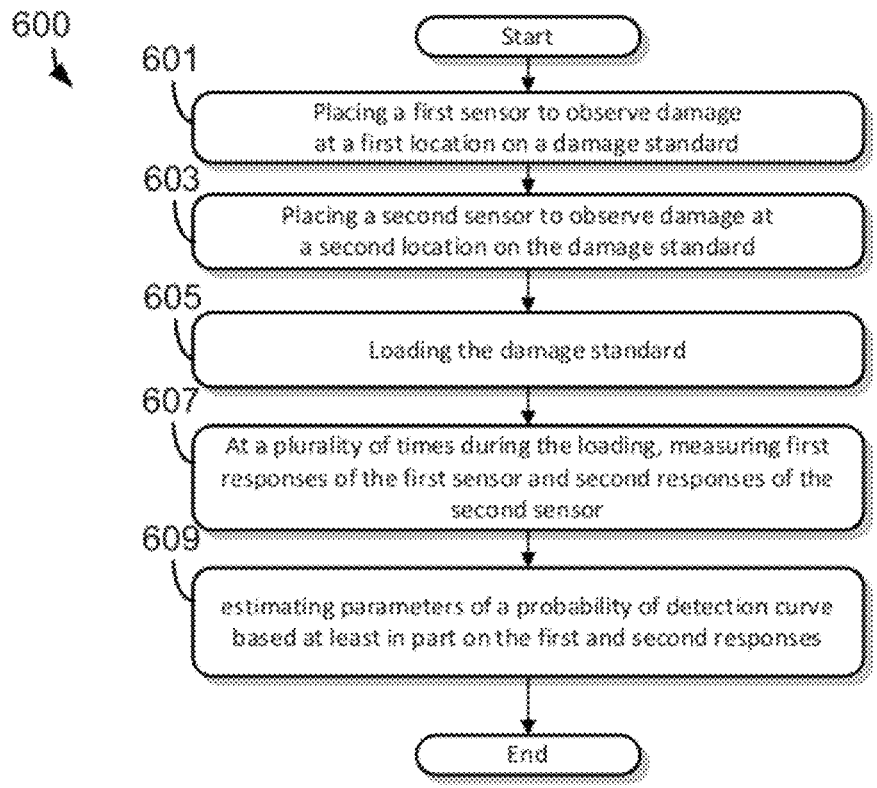
FIG. 6A is a flow diagram of a method for generating a performance curve using an NDT system according to some embodiments.

Attention is now turned to FIG. 6A which shows a flow diagram for a method 600 for generating a performance curve with an NDT system.

Figure 6B:
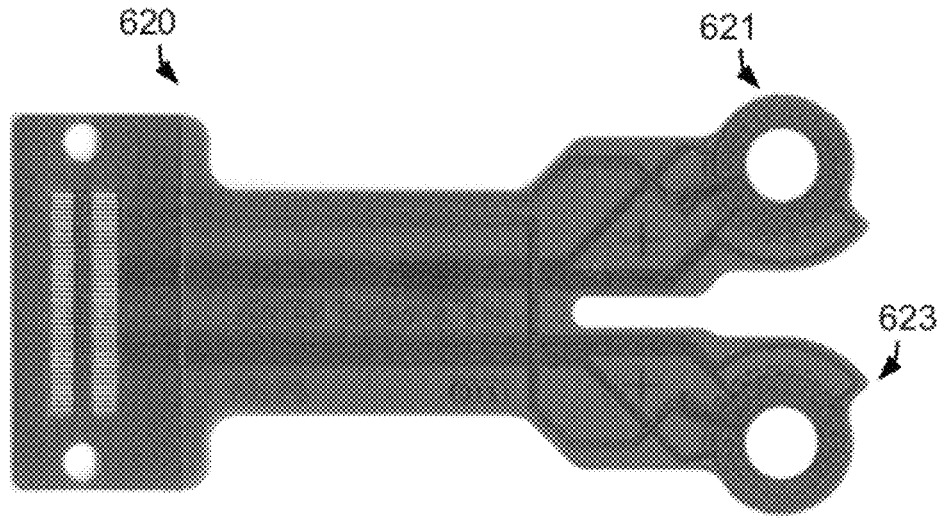
FIG. 6B is an integrated sensor that may be used with the NDT system according to some embodiments.

At step 601 a first sensor is placed to observe damage at a first location on a damage standard. At step 602 a second sensor is placed to observe damage at a second location on the damage standard. The first and second sensor may be placed in any suitable way. For example, the sensors may be mounted to the damage standard, held in place by a fixture, or mounted on a fixture for scanning the respective locations on the damage standard. In some embodiments the first and second sensor are integrated sensors such as integrated sensor 620, shown in FIG. 6B. Sensor 620 has a first eddy current sensor 621 and second eddy current sensor 623. The sensor may be adapted for the target component and/or damage standard geometry. For example, integrated sensor 620 may be adapted for the damage standard 500 (FIG. 5A).

In some embodiments the first and second sensors are substantially identical. That is, the sensors are of the same design and manufactured with tolerances such that they give substantially the same response (when calibrated, if necessary) to within the requirements of the target application.

In some embodiments, one or both of the first and second sensors are oriented to observe damage in material adjacent to a hole in the damage standard. The sensors may each have two or more sensing elements. Sensing elements may be positioned on opposite sides of the hole near regions where high stress is anticipated when the damage standard is loaded. For example, on the edges of the bolt hole transverse to the loading direction (at 3 and 9 o'clock if the sensor is loaded from 6 and 12 o'clock).

Figure 6C:
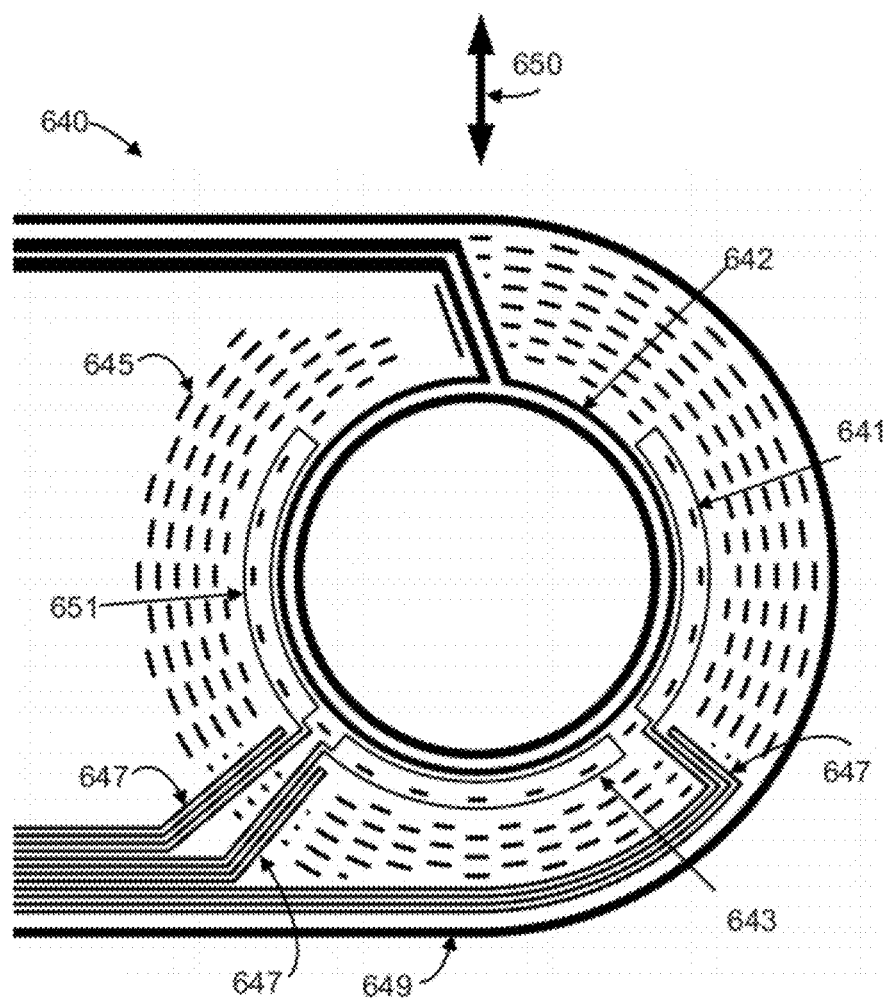
FIG. 6C is a sensor that may be used with the NDT system according to some embodiments.

Sensor 640, in FIG. 6C, is an example of a "rosette" eddy current sensor. Sensor 640 has a drive winding 642 to impose a magnetic field in the damage standard. Sensing elements 641 and 651 provide sensitivity to cracks in the high-stress regions of the damage coupon when the damage standard is loaded along axis 650. Sensor 640 may include a sensing element 643 in a lower stress region to be used as a reference aiding calibration, temperature and drift compensation, and trouble shooting. Sensor 640 may include other features such as durability enhancing pillars 645 and flux cancellation leads 647, which are described, for example, in U.S. Patent Publication No. 2011/0210724 titled "Durability Enhanced and Redundant Embedded Sensors" by Goldfine et al. and is incorporated by reference in its entirety.

At step 605 the damage standard is loaded. The loading may, for example, be static, dynamic, or applied in any suitable way. The loading may be a sequence that includes periods of static and dynamic loading. For example, the loading may be dominated by cyclical loading with intermittent periods where the load is static or a spectrum loading may be used.

At step 607, at a plurality of times during loading (step 605), the responses of the first and second sensor are recorded. The raw sensor responses may be recorded at multiple frequencies and process to provide material properties characterizing the damage. For example, sensor impedance data at multiple frequencies may be used to estimate crack depth (which may be used as a-hat data for step 609).

If properly placed at steps 601 and 603, the sensor will respond to damage forming at the respective locations being observed by the sensors on the damage standard. In some embodiments, the damage is cracking. Though, any suitable damage mode may be observed. The responses may be recorded at a sufficient rate that the change in load experienced by the damage standard during measurement may be ignored. By recording each sensor response in connection with a specific degree of loading of the damage standard, enhanced damage observability may be achieved. In some embodiments the sensor responses are recorded during a static loading period of the loading process.

At step 609, parameters of a performance curve are estimated based at least in part on the responses of the first and second sensor recorded at step 607.

Figure 7A:
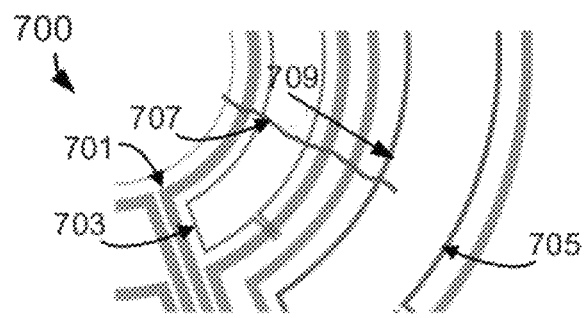
FIG. 7A is a detail of a sensor with multiple sense elements for obtaining a substantially linear sensor response to damage growth in a damage growth direction according to some embodiments.
Figure 7B:
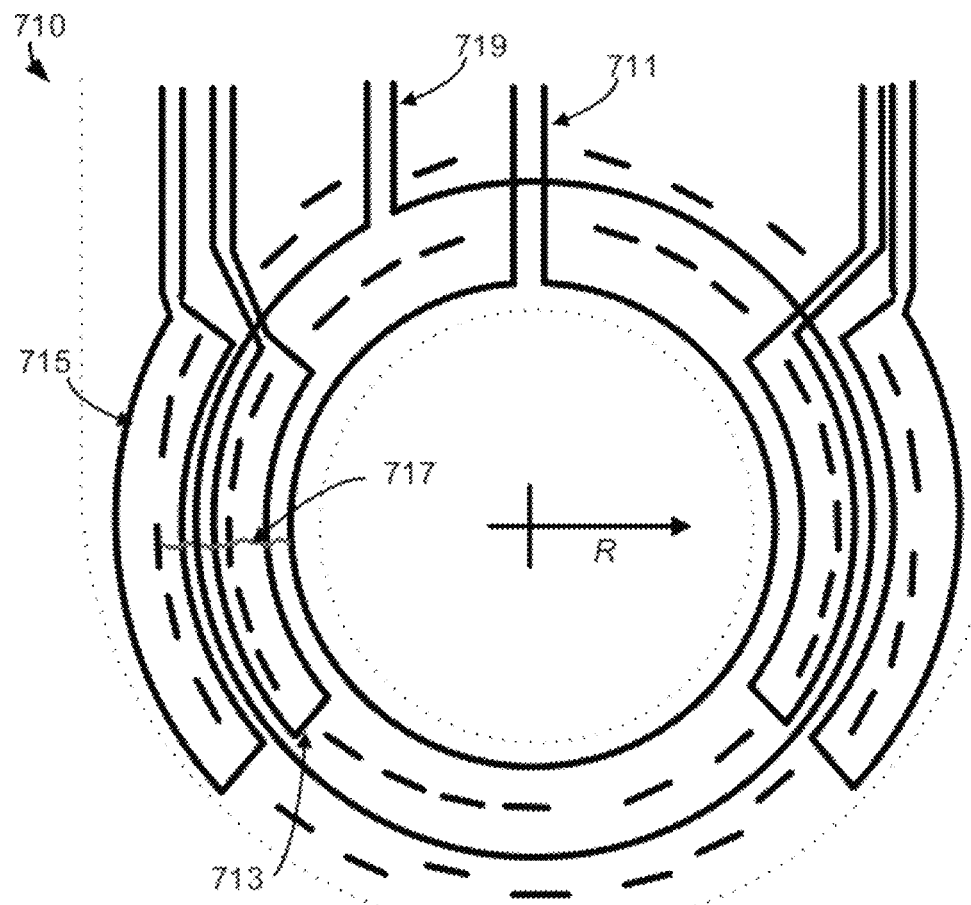
FIG. 7B is a sensor with multiple drive and sense elements for obtaining a substantially linear sensor response to damage growth in a damage growth direction according to some embodiments.

Having discussed some methods in which NDT system 100 may be used, attention is now turned to FIG. 7A which shows, in relevant part, an eddy current sensor 700 which may be used, for example, as part of NDT system 100. Sensor 700 has a drive winding 701, and sensing elements 703 and 705. Sensor 700 may be placed proximal to a test part such that damage 707 growing in direction 709 will produce a substantially linear response from sensing elements 703 and 705 over substantially abutting damage sizes. It should be appreciated that obtaining a linear sensor response includes the possibility of transforming the sensor response data, for example but not limitation, taking the logarithm of the response. FIG. 7B shows another example of an eddy current sensor 710, with drive windings 711 and 719, and sense elements 713 and 715 to detect damage 717. Note that sensor 710 may comprise multiple layers to prevent electrical shorting between the windings; specifically, drive 719 is simply superimposed and need not be electrically shorted to the leads of other sense elements, drive windings. Drive windings 711 and 719 may be connected in series such that the currents are in the same or opposite directions. In some embodiments, drive windings 711 and 719 are independently driven by the instrumentation or have a switching mechanism so that the different driving modes may be used.

In some embodiments, sensing elements are provided in all four cardinal direction, or in any suitable increment to provide sufficient resolution at locations that may or are likely to be damaged. Sensors may also be stacked with different orientations with respect to on another to provide, for example, redundancy and improved sensitivity.

Figure 7C:
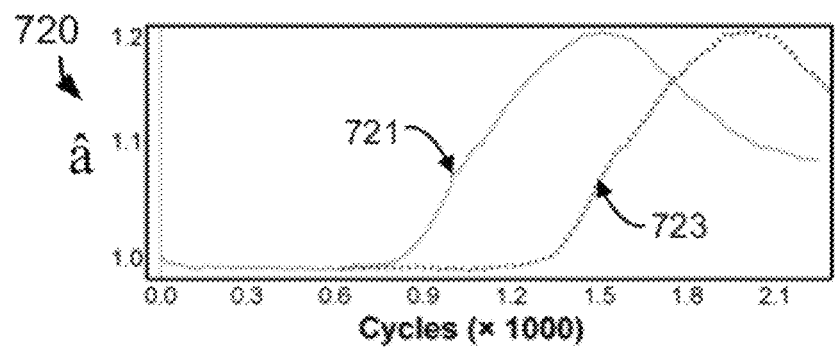
FIG. 7C is a plot illustrating an example of the sensor element responses from a sensor configured to obtain a substantially linear sensor response to damage growth in a damage growth direction.

Plot 720 in FIG. 7C illustrates the characteristic behavior of sensor 700 during damage evolution. Damage 707 initiates and grows during the test. As the damage grows, a response 721 of sensing element 703, which is closer to the damage initiation site, begins to change. As the damage continues to propagate, eventually sensing element 705's response 723 also begins to respond to the damage.

Figure 7D:
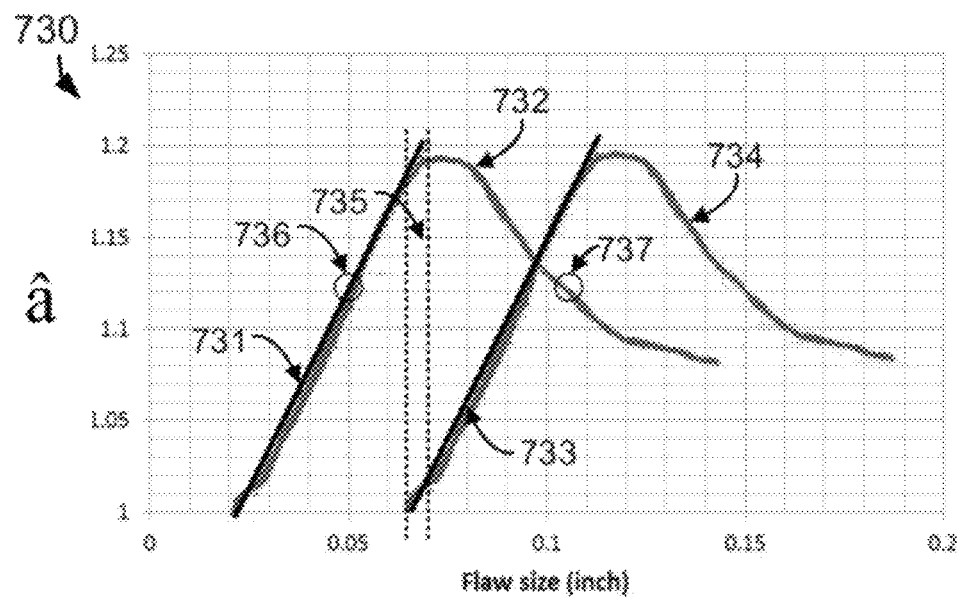
FIG. 7D is a plot illustrating the substantial linearity of the sensor response to damage size over two sensing elements.

Plot 730, shown in FIG. 7D, illustrates conceptually the â versus a data from a damage evolution test of sensor 700. The ground truth data, "a", may be obtained in any suitable way. For example, ground truth may be captured intermittently by direct measurement and intervening ground truth values may be estimated using a suitable damage growth model. The â versus a data for sensing element 703 is shown by curve 732. The â versus a data for sensing element 705 is shown by curve 734. Curve 732 has a substantially linear region indicated by line 731 that covers a range of lower damage sizes (smaller "a" values). Similarly, curve 734 has a substantially linear region indicated by line 733 that covers a range of larger damage sizes (larger "a" values). The linear regions of sensor response for sensing element 703 and 705 substantially abut. That is, damage sizes that exceed the region where sensing element 703's response 712 is linear are approximately large enough so as to be in the linear region of sensing element 705's response 723. Depending on the properties of sensor 700 and the mode and direction of damage propagation, the linear regions may overlap more or less, or be slightly disjoint.

It should be appreciated that the sensor response from one sensing element alone of sensor 700 may be ambiguous. For example, a response of â=1.12 from sensing element 703 could indicate a damage size of 0.05 in. or 0.105 in. The ambiguity may be resolved, for example, by using historical information of the sensor response or the response from sensing element 705.

The sensor responses may be combined in a suitable way to estimate a performance curve for sensor 700. For example, instrument 110, shown in FIG. 1, may be used. It should be appreciated that the variance for damage size estimates produced may be larger in circumstances where the linear region of sensing element responses is slightly disjoint. Likewise, the variance for damage size estimates may be smaller in circumstances where the linear region of sensing element responses is overlapping.

Figure 8A:
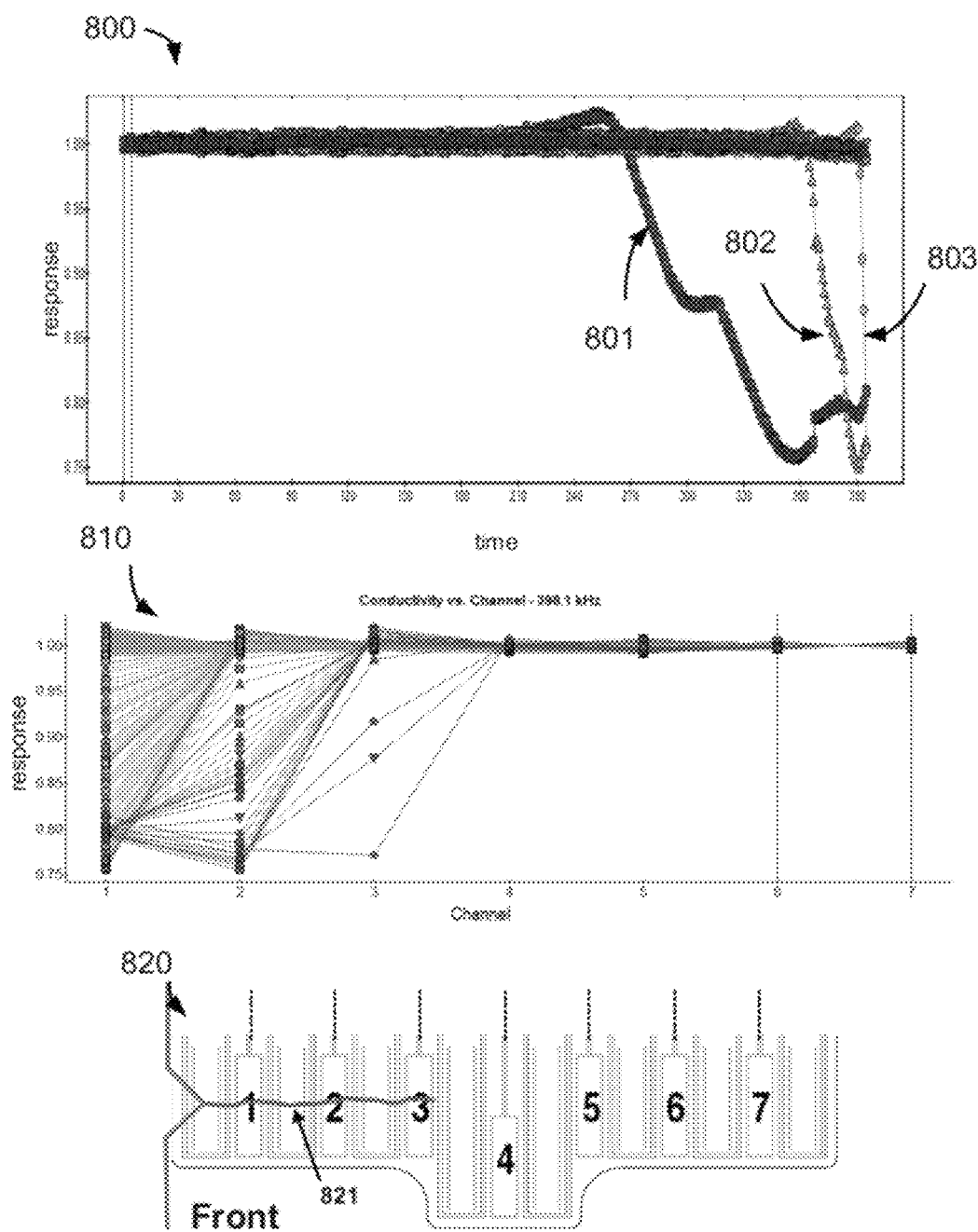
FIG. 8A shows a sensor for obtaining a sensor response to damage growth in a damage growth direction and plots illustrating the sensor response as it is continually monitored during damage growth according to some embodiments.
Figure 8B:
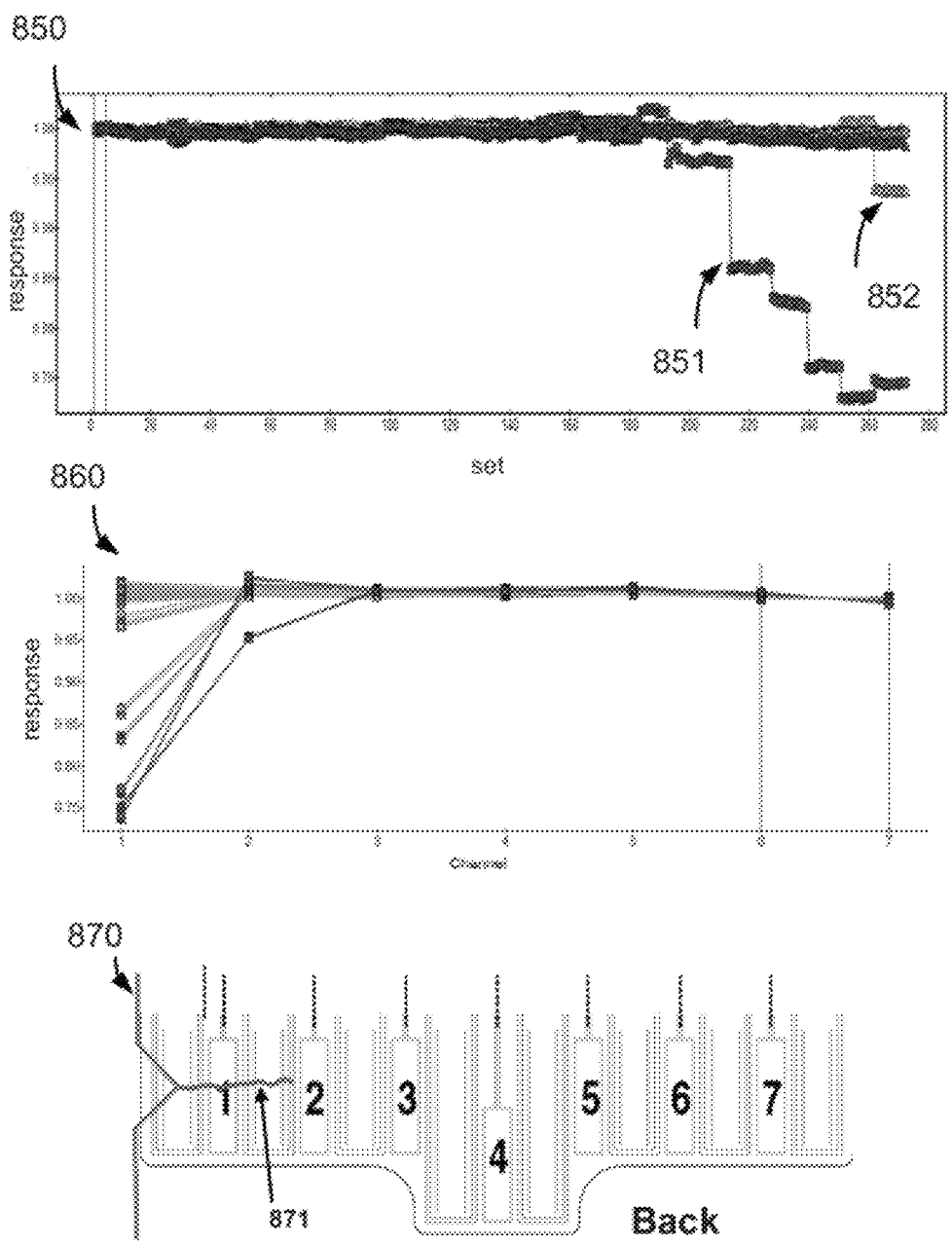
FIG. 8B shows a sensor for obtaining a sensor response to damage growth in a damage growth direction and plots illustrating the sensor response as it is intermittently monitored during damage growth according to some embodiments.

Other aspects of such a sensor design are described now in connection with FIGS. 8A-8B. Specifically, FIG. 8A shows data collected from a sensor 820 mounted to the front side of a test part and FIG. 8B shows data collected from a sensor 870 mounted to the back side of a test part. Both sensors 820 and 870 have a linear configuration. Here 7 sensing elements are shown, but this is merely illustrative and any suitable number of sensing elements may be used.

In FIG. 8A plots 800 and 810 show sensor 820's response to damage 821. In plot 800 the sensor response of each sensing element is plotted as a function of time into the damage evolution test. Responses 801, 802 and 803 correspond to sensing elements 1, 2 and 3 respectively. The response of channels 4-7 does not change substantially during the damage evolution test. Plot 810 shows the same data plotted as a function of channel for select times.

FIG. 8B shows plots 850 and 860 of sensor 870's response to damage 871. Plot 850 is similar to plot 810 except that responses were recorded in multiple "sets" after substantial intervals in time during the damage evolution test. The result is a discrete stair-like shape that simulates what the response of the sensor may look like over time in a fielded application where NDT may only be performed intermittently, for example, when an aircraft is on the ground or at a maintenance depot.

Sensors 700, 820 and 870 are illustrative embodiments of sensor 120 of NDT system 100. Sensor 700 (820 and 870) may be any suitable type of sensor technology and may have any suitable geometry such a linear geometry or a radial geometry. Sensing elements 703 and 705 may be the same size or may change size (e.g., increase or decrease) or shape in accordance with the test part geometry and anticipated damage modality. For example, sensing elements 703 and 705 may be concentric with sensing element 703 at a smaller radius than element 705. Sensing element 705 may be proportionally larger than 703 or may have a different shape to maintain the same sensing element area. Similar sensing element sizes may be useful in permitting the sensing electronics to be identical or to permit sensing electronics to be multiplexed for the two elements. Note that if one sensing element receives a substantially larger sensor response a different instrument configuration may be required. For example, a different amplifier gain may be required. It should also be appreciated that while a sensor with 2 sensing elements for monitoring a single damage propagation path were described in connection with sensor 700 and 7 sensing element were described in connection with sensors 820 and 870, any suitable number of sensing elements may be used. Note also that in FIG. 6B a second or third additional concentric drive loop may be included between or beyond the second sensing element. The added drive loops may carry current in the same or opposite direction.

The test part to which the sensor is proximally located may be any suitable test object such as a damage standard, a component, subcomponent, and the like. In some embodiments, the test part is a component of an aircraft.

These sensors may be flown on an aircraft at any number of fatigue critical locations. During a validation and verification phase, sensor data is acquired when the aircraft is on the ground, in the air, or both. This could be accomplished over a sufficient period of time to provide sufficient detection confidence at representative noise levels. Such sensor data could be augmented with ground truth data or usage data and recorded to a database for performance curve generation consistent with the described methods. Data without damage may be used to estimate confidence intervals and predict false indication rates.

In some embodiments, the damage standard is dynamically loaded, for example, in low-cycle fatigue or high-cycle fatigue. The loading may be intermittently paused to permit ground truth data to be obtained. The intermittent ground truth data may be provided to a damage evolution model to estimate ground truth data during the intervening periods of the damage evolution test. Thus, the NDT system data obtained during the test combined with the actual ground truth data and the estimated ground truth data creates substantially more datasets for the â versus a database than conventional approaches. In one such embodiment, confidence is improved by including such estimated data.

Having discussed various aspects with connection with the figures, some further aspects are now described.

One aspect relates to a method and apparatus for performance curve generation and enhancement for stationary, non-destructive testing (NDT) sensors that monitor a defined area of a material under test (MUT). In some embodiment, a statistical representation of performance such as a probability of detection (POD) curve is generated. Though, any suitable curve for characterizing the performance of an non-destructive testing sensor may be used. The feature sought to be detected may be a flaw in the MUT. The flaw may be any type of deviation from ideal MUT conditions. The flaw may be caused by material fatigue, impact damage, manufacturing variation, or any other source. In some embodiments, the flaw is a crack, residual stress relaxation, composite fiber and/or matrix damage, impact damage, or any other suitable type of flaw or combination of flaws.

A crack response database comprising a set of self-consistent crack response versus crack size data is generated using suitable test articles such as coupons, subcomponents or other test article, or combination of test articles. The crack response is the response of the crack measured by the NDT sensor while the crack size is determined independently from the NDT sensor measurement. The sensor configuration intended for use in-service may be used to develop the crack response database. The goal in preparing the crack response data is to minimize the number of tests required to accumulate the data while at the same time being sufficient to produce practical performance curves with confidence intervals an to predict false indication rates that bound performance within the practical limits of the relevant arts.

A methodology separate from the NDT sensor is used to characterize the flaw. For example, the methodology may be striation counting, beach marking, acetate replication for determining crack size (length and/or depth) and fractography. Though, any suitable method may be used. Of course, the methodology used may depend on the type of flaw and the way the flaw is being characterized. The accuracy and intervals at which the separate methodology is provided must be sufficient to bound the confidence intervals as may be required by the particular application. In some embodiments, a crack growth model is used to improve confidence in the crack sizing data and to fill in between the results of the separate crack size measurements.

A non-destructive testing sensor such as an MWM-Rosette or linear MWM-Array may be placed over (near or attached to) a fatigue critical region of a test article and data may be recorded either continuously or at intervals. Intervals may be chosen in any suitable way, for example, they may be scheduled as uniform or non-uniform in time or cycles.

The NDT response is converted into a measure of a crack (or other damage, e.g., corrosion) dimension/feature. The method includes a means for converting data from multiple test articles into a POD curve or other statistical performance measure. In some embodiments, data from damage standards, subcomponents, and in-service data, or any combination thereof are used to generate a POD curve confidence intervals and/or false indication rates.

In another embodiment, the NDT sensor is intentionally modified to alter the shape of the performance curve. In one such embodiment, a second channel is added to an MWM-Array in the direction of crack growth (e.g., an outer element in a rosette beyond the inner element). The purpose of the element is to produce continual observability of the monotonic crack growth producing crack response vs. crack size data that meet predetermine performance curve generation criteria and/or provide improved curve features. In one such embodiment, the improved curve feature is the steepness of the transition from low POD to high POD. In another embodiment, the enhancement is a more linear crack response vs. crack size data set with constant variance over the crack size range of interest.

In some other embodiments, multiple identical feature are included within a test article to enable generation of more crack response vs. crack size data from a single test at a lower cost. Another embodiment, is the intentional inclusion of noise and other crack response influencing variations in the test articles to better represent the statistical nature of the application. In one such embodiment, EDM starter notches at different locations might be included. In another, temperature, loads, material properties, or other test conditions might be varied to capture representative in-service conditions that contribute to variation in response.

The test samples with known crack sizes may be retained for future POD curve generation/studies.

One aspect relates to a method of generating a probability of detection curve where the parameters of the curve are estimated using a damage standard: placing at least one sensor and monitoring the sensor response to the damage level as the damage standard is loaded to initiate and grow the damage of interest at a location observed by the at least one sensor; and repeating this process for a sufficient number of damage standards to provide a sufficient confidence level in the estimation of at least one parameter of the probability of detection curve. The number of standards may be based on satisfying the confidence level required. The sufficient confidence level may be predetermined based on a risk analysis for the intended application. The intended application, for example, may be risk based life management of a critical component using remaining life estimation that includes the non-destructive testing method represented by the POD curve. In some cases the parameter of interest is the damage level at the 90% probability of detection point in the curve that has an associated 95% confidence level. In some cases the damage is a fatigue crack and the coupon is loaded cyclically at a predetermined load level that is representative of the component of interest damage formation. In some cases the data from the damage coupon is combined with additional damage sensing data to improve the probability of detection curve suitability for life management of a component of interest. The additional damage sensing data is actual nondestructive testing results from field service components using essentially the same inspection procedure and sensor used on the damage coupons. The additional data may be from a more complex subcomponent that represents the actual component of interest. Though, the addition data may be from any suitable source.

Another aspect relates to a method for performing a probability of detection study where at least one damage standard is generated with at least two sensors located to observe damage for at least two different predetermined locations on the damage standard, where the data from the sensor response taken at a plurality of times during the damage evolution testing and for each of the two locations is used to estimate the parameters of a probability of detection curve, where the sensor format used is essentially identical to the intended use for in service monitoring of a critical component. The damage evolution may be a crack and data is recorded only when the load is static. In another case the damage evolution may be a crack and data is recorded during loading with a sufficient data acquisition rate to segment the recorded data based on the degree of loading to enhance the observability of the crack behavior. (At higher load a crack may be more open which may result in a larger sensor response.) Though, any suitable form of damage evolution may be tested. The sensor may be an eddy current sensor and the data may be recorded at a plurality of times during the damage standard testing as the damage initiates and grows and where the two different predetermined locations are essentially identical in geometry and anticipated damage behavior. In some embodiments, the sensor has at least two sensing elements that provide independent sensor to crack combinations on different segments of a single geometric feature. The geometric feature may be a hole (such as in a metal coupon) and the sensing elements are at 3 o'clock and 9 o'clock to monitor the growth of discrete cracks on opposite sides of the hole. The location may be a curved surface that experiences higher stresses on a metal coupon. Though, the sensors may be placed at any suitable locations.

Yet another aspect relates to a method of sensing damage using at least one sensor with at least one field source and at least two sensing elements mounted to a test part, where the sensor locations are selected to monitor damage growth along a growth path, and the locations are selected to extend the approximately linear region of the sensor damage response when plotted verses actual damage level so that a quantitative performance evaluation can be performed for the multiple sensor configuration where said extension is significantly beyond the approximately linear region when only one sensing element is provided along an anticipated damage growth path. In some cases the sensing method and sensor design and data analysis also provides a sufficiently uniform variance over the linear region of the sensor damage response vs. actual damage level relationship. In some embodiments the sensing element are the same size. This may permit, for example, the same gain level to be used. The sensing elements may be positioned so that a first sensing element continues to respond to the damage growth at least until the second element begins to respond to the continuing damage growth. The sensing elements may be positioned as far as part as possible to reduce the number of sensing elements required to cover the crack growth path of interest and where the POD curve confidence in regions between sensing elements is noted to be lower than closer to the sensing elements. In some embodiments two different sensing element formats are used to capture different segments of the crack growth path. A first segment may be around a hole to detect small crack growth and a second segment may be near a radius away from the hole to observe that the crack has reached a fatigue critical radius and the POD curve applicability and the curve itself are adjusted for each segment of the crack growth path. The sensing elements may be larger at larger radii from the hole cover the likely crack growth path. Accordingly, the electronics is designed to enable measurement from sensors with such variously sized element. In some embodiments, the at least one sensor is an eddy current sensor with at least one drive and at least two sensing elements. In some embodiments the at least one sensor is an ultrasonic sensor with at least one excitation source and two receivers. In some embodiments, the eddy current sensor is a rosette format with at least two sensing elements located at different distances from a hole where a crack is likely to initiate. In some embodiments, the at least two sensing elements are observing the same location to provide redundancy. The redundancy may provide improved confidence in performance. The redundancy may enable data to be acquired even if one sensing element has failed to operate properly. In some cases multiplexing electronics is used to sample data from multiple sensors. In some other embodiments, parallel cabling with multiple electronics channels are used to acquire data from the sensors. In other cases a combination of multiplexing and parallel cables/data processing are used. In some cases the NDT instrument to collect data is plugged in to acquire data and then detached and reattached at a later time to emulate in-service inspection conditions and the sensor is left in place between data acquisitions. The sensors may be flown on an aircraft at fatigue critical locations and during the validation and verification phase sensor data is acquired when the aircraft is on the ground only, and this is accomplished over a sufficient time period and for multiple sensors at multiple locations on multiple aircraft to generate probability of detection curve with sufficient confidence and representative noise levels to achieve approvals of the decision authorities for use on service aircraft. Noise sources may be intentionally introduced to determine the bounds of performance and assess the sensor robustness. The sensor may be a rosette type sensor mounted outside of the fastener head or collar. The sensor may be mounted between surfaces of the material under test. Thin sensors, for example under 5, 10, 20 or 50 mils thick (or any other suitable thickness) may be used for such an application.

Still another aspect relates to a method for generating a performance curve for a damage detection sensor, where a software algorithm combines data from two or more damage locations on one or more coupons, said data includes at least two sensor-damage combinations, the software algorithm estimates the parameters of the performance curve and the confidence intervals associated with the performance curve, the sensor data is acquired at multiple times during the testing of at least one damage specimen, the software estimates a feature of the sensor response that is correlated with a feature of the damage of interest, the sensor data is spatially registered at each of the two or more damage locations, the feature of the sensor response that is correlated with the damage of interest is derived from sensor data at two or more different times during the testing. The sensor may be physically moved across the part to generate a spatially registered data set in at least one dimension and where datasets at each time are spatially synchronized. The spatial synchronization may be accomplished by shifting the dataset at one time in at least one spatial direction relative to the dataset at another time using common spatial features in both datasets. The data may be synchronized in loading as well as spatially such that data at each time is taken at one or more static loads with the damage evolution loading stopped. Data at two different loads may be combined (e.g., in a manner such as subtraction) before data is compared at different times. In some embodiments, a pervious sensor response is subtracted from a later sensor response and then the feature of the sensor response that is correlated with the damage of interest is derived from the resulting difference response. In some embodiments, an eddy current sensor is permanently installed at each damage location. In some embodiments, the eddy current sensor is scanned across the damage locations to acquire spatially registered sensor response data.

Another aspect relates to a system for generating performance curves. The system includes a test part, a plurality of additional test parts for recording the response of a plurality of additional, essentially identical sensor under essentially identical conditions and a sensor proximal to the test part for monitoring damage size. The system also includes equipment for recording the sensor response at a plurality of known damage sizes as the damage grows and for combining the damage-sensor combinations for a plurality of damage sizes and sensor pairs, and for generating a performance curve and associated performance statistics to assess the effects on performance of damage size and sensor visibility. The sensors may be eddy current sensors. The performance curve may be a POD curve and the damage may be a crack. Ground truth data may be recorded by periodically stopping the test and taking acetate replicas with and without a static load. The number of damage standards tested may be determined by the confidence in the resulting performance curve.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of generating a probability of detection (POD) curve, the method comprising acts of:
   (a) placing a sensor proximal to a damage standard, the sensor having a drive, primary winding and at least two sensing, secondary windings, the at least two secondary windings located in spatial increments along a damage growth path on the damage standard;
   (b) dynamically loading the damage standard to initiate and grow damage of interest along the damage growth path;
   (c) exciting a current on the primary winding and measuring a plurality of monotonic responses on each of the at least two secondary windings during the loading;
   (d) suspending the dynamic loading at a plurality of times and, during each such suspension, measuring ground truth data for the damage of interest; and
   (e) generating the POD curve based at least in part on the plurality of responses from each of the at least two secondary windings during the loading and on the ground truth data;

wherein: the at least two secondary windings of the sensor comprise a first secondary winding and a second secondary winding,
the plurality of responses include a first response of the first secondary winding and a second response of the second secondary winding, and
act (e) comprises combining the first response and second response into a combined response that is substantially linear with respect to damage level, and the combined response and the ground truth data are used to generate the POD curve, wherein substantially linear is defined with reference to FIG. 7D as at least as linear as the data (734) in the substantially linear region (733).

2. The method of claim 1, further comprising acts of:
defining an acceptable confidence based criterion for at least one parameter of the POD curve;
repeating acts (a), (b), (c) and (d) for a plurality of damage standards to satisfy the acceptable confidence based criterion for at least one parameter of the POD curve; and
verifying the acceptable confidence based criterion for the at least one parameter of the POD curve is met or exceeded.

3. The method of claim 2, wherein the acceptable confidence based criterion is predetermined based on a risk analysis for an intended application of the POD curve.

4. The method of claim 3, wherein the intended application is risk based life management of a critical component using remaining life estimation that includes a non-destructive testing method represented by the POD curve.

5. The method of claim 2, wherein the at least one parameter comprises a damage level at a 90% probability of detection point in the POD curve that has an associated 95% confidence level.

6. The method of claim 1, wherein the damage of interest is a fatigue crack, and loading is cyclical at a predetermined load level that is representative for a component of interest.

7. The method of claim 1, wherein the ground truth data is obtained by an acetate replica.

8. The method of claim 1, wherein the ground truth data is augmented by estimating ground truth using a damage growth model and the ground truth data.

9. The method of claim 1, wherein the first response is substantially linear for a first range of smaller actual damage levels, and the second response is substantially linear for a second range of larger actual damage levels, and the substantially linear first range for the first response overlaps the substantially linear second range for the second response.

10. The method of claim 1, wherein the at least two secondary windings of the sensor are a same size.

11. The method of claim 1, wherein:
the at least two sensing elements comprise a first secondary winding and a second secondary winding, and
the act (a) comprises placing the sensor near a hole on the damage standard such that the first secondary winding is at a first radius from the hole and a second secondary winding at a second radius from the hole larger than the first radius.

12. The method of claim 11, wherein the second secondary winding is larger than the first secondary winding in proportion to the second radius relative to the first radius.

13. A method of generating a probability of detection (POD) curve, the method comprising acts of:
   (a) placing a sensor proximal to a damage standard, the sensor having a drive, primary winding and at least two sensing, secondary windings, the at least two secondary windings located to monitor damage growth in spatial increments along a damage growth path on the damage standard;
(b) dynamically loading the damage standard to initiate and grow damage of interest along the damage growth path;
(c) exciting a current on the primary winding and measuring a plurality of monotonic responses on each of the at least elements secondary windings during the loading;
(d) measuring ground truth data for the damage of interest at a plurality of times during the loading;
(e) generating the POD curve based at least in part on the plurality of responses from each of the at least two secondary windings during the loading and on the ground truth data;
(f) defining an acceptable confidence based criterion for at least one parameter of the POD curve, the acceptable confidence based criterion defined based on a risk analysis for risk based life management of a critical component using remaining life estimation that includes a non-destructive testing method to be represented by the POD curve;
(g) repeating acts (a), (b), (c) and (d) for a plurality of damage standards to satisfy the acceptable confidence based criterion; and
(h) verifying the acceptable confidence based criterion is met or exceeded, wherein acts (a), (b), (c) and (d) are repeated on field service components and the generating in act (e) is further based on results from the field service components;
wherein: the at least two secondary windings of the sensor comprise a first secondary winding and a second secondary winding,
the plurality of responses include a first response of the first secondary winding and a second response of the second secondary winding, and
act (e) comprises combining the first response and second response into a combined response that is substantially linear with respect to damage level, and the combined response and the ground truth data are used to generate the POD curve, wherein substantially linear is defined with reference to FIG. 7D as at least as linear as the data (734) in the substantially linear region (733).

14. A method of generating a probability of detection (POD) curve, the method comprising acts of:
(a) placing an eddy current sensor proximal to a damage standard, the eddy current sensor having a drive, primary winding and at least two sensing, secondary windings, the at least two secondary windings located in spatial increments along a damage growth path on the damage standard;
(b) dynamically loading the damage standard to initiate and grow damage of interest along the damage growth path;
(c) exciting a current on the primary winding and measuring a plurality of monotonic responses on each of the at least two secondary windings during the loading;
(d) measuring ground truth data for the damage of interest at a plurality of times during the loading; and
(e) generating the POD curve based at least in part on the plurality of responses from each of the at least two sensing elements secondary windings during the loading and on the ground truth data, wherein the eddy current sensor is placed at a fixed position throughout acts (b) and (c);
wherein: the at least two secondary windings of the sensor comprise a first secondary winding and a second secondary winding,
the plurality of responses include a first response of the first secondary winding and a second response of the second secondary winding, and
act (e) comprises combining the first response and second response into a combined response that is substantially linear with respect to damage level, and the combined response and the ground truth data are used to generate the POD curve, wherein substantially linear is defined with reference to FIG. 7D as at least as linear as the data (734) in the substantially linear region (733).

* * * * *